United States Patent [19]

Renganathan et al.

[11] Patent Number: 6,071,712
[45] Date of Patent: Jun. 6, 2000

[54] ENZYMATIC PROCESS FOR THE PRODUCTION OF CEPHALOSPORINS

[75] Inventors: Vedanthadesikan Renganathan, Portland, Oreg.; Martin Brenner, Havertown, Pa.

[73] Assignee: SmithKline Beecham Corporation, Philadelphia, Pa.

[21] Appl. No.: 08/933,517

[22] Filed: Sep. 18, 1997

Related U.S. Application Data

[62] Continuation of application No. 08/550,728, Nov. 1, 1995, abandoned, which is a continuation of application No. 08/308,866, Sep. 19, 1994, abandoned, which is a continuation of application No. 08/129,047, filed as application No. PCT/US92/02781, Apr. 6, 1992, abandoned.

[51] Int. Cl.[7] ...................................................... C12P 35/00
[52] U.S. Cl. ......................... 435/47; 435/117; 435/254.3; 435/911
[58] Field of Search .......................... 435/47, 117, 254.3, 435/911

[56] References Cited

U.S. PATENT DOCUMENTS

| 4,053,360 | 10/1977 | Bouzard | 435/47 |
| 4,141,790 | 2/1979 | Niwa | 435/47 |
| 4,347,314 | 8/1982 | Cole | 435/43 |

OTHER PUBLICATIONS

The Merck Index, 10th ed., p. 269, 1983.

*Primary Examiner*—Irene Marx
*Attorney, Agent, or Firm*—Janice E. Williams; Charles M. Kinzig

[57] ABSTRACT

An enzymatic process for hydrolyzing the 7-position acyl ester of certain cephalosporin compounds to the corresponding alcohol is disclosed.

11 Claims, No Drawings

ENZYMATIC PROCESS FOR THE PRODUCTION OF CEPHALOSPORINS

This is a continuation of application Ser. No. 08/550,728 filed Nov. 1, 1995, now abandoned, which is a continuation of Ser. No. 08/308,866 filed Sep. 19, 1994, now abandoned, which is a continuation of Ser. No. 08/129,047 filed Oct. 4, 1993, now abandoned, which is the 35 USC §371 National Stage entry of PCT International Application No. PCT/US92/02781, filed Apr. 6, 1992.

BACKGROUND

This invention relates to a process for the production of the antibiotic of formula (A),

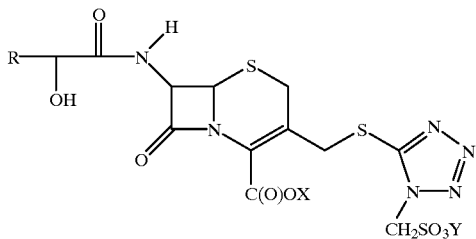

where R is any group which gives a compound having antibacterial activity and X is hydrogen or a pharmaceutically acceptable cation and Y is a pharmaceutically acceptable cation.

A subgroup of compounds of formula A (one is sold commercially under the name "Monocid") are disclosed in two U.S. Pat. Nos. 4,048,311 and 4,576,937. The monosodium salt of the sulfomethyl group is specifically described and claimed in the later '937 patent. The antibacterial activity of these compounds is described in U.S. Pat. No. 4,048,311 (see column 6, line 19 to column 9, line 49 and the data in Tables 1 and 2).

The '937 patent discloses a chemical synthesis for certain of the compounds of formula A, particularly the salts such as the sodium salt. That process comprises reacting a compound of formula (B)

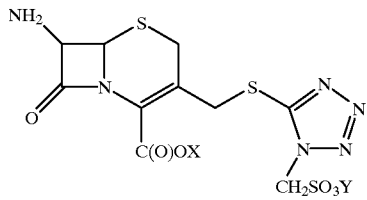

with inter alia O-formylmandelic acid to produce a formyl intermediate of formula (C).

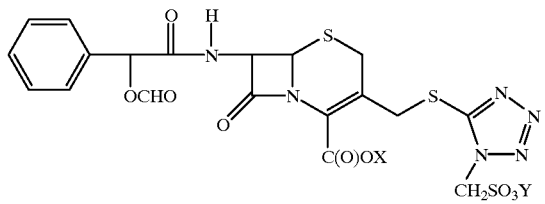

Alkali hydrolyzes the —OCHO group giving the corresponding alcohol of formula (D),

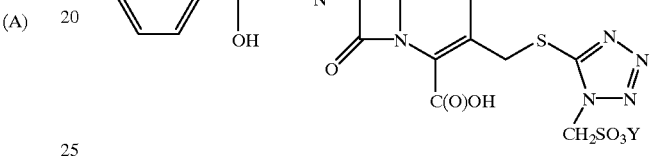

a compound called cefonicid sodium where X and Y are sodium, in 80 to 85% yield. The decreased product yield is possibly due to the degradation of both the formyl intermediate (C) and cefonicid sodium by alkali. Hydrolysis at neutral or mildly acidic conditions increases the stability of (C) and the resulting cefonicid salt but decreases the hydrolysis rate significantly. An alternative more efficient procedure was needed.

Hydrolases such as lipases, esterases, and amidases are employed in the stereospecific and regiospecific hydrolyses of ester and amide linkages. The biological function of lipases is to catalyze the hydrolysis of triacylglycerol to the corresponding fatty acid precursors and glycerol. Lipases are not known to hydrolyze an ester linkage which is part of a cephalosporin nucleus as in (C). Esterases hydrolyze soluble carboxylic acid esters to the corresponding acid and alcohol precursors. Esterases from *Escliericliia coli, Pseudomonas aeruginosa, Aspergillus niger* and Saccharomyces sp. hydrolyze ester linkages (U.S. Pat. No. 4,346,168) in which the carboxyl group is bonded to a penicillin of the formula (E),

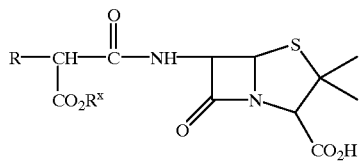

where $R^x$ is an alkyl, aryl, or arylalkyl group.

However, (C) is structurally different from (E). The current knowledge of lipases and esterases does not predict that any of these enzymes will be able to hydrolyze the formyl intermediate of the cephalosporins of this invention as illustrated by formula (C).

The object of the work leading to this invention was to find out whether a hydrolase-dependent enzymatic process would transform the formyl intermediate (C), or another such cephalosporin ester, to cefonicid sodium in quantitative yield in the pH range of about 3.5–8.0.

SUMMARY OF THE INVENTION

This invention relates to a process for preparing a compound of formula I,

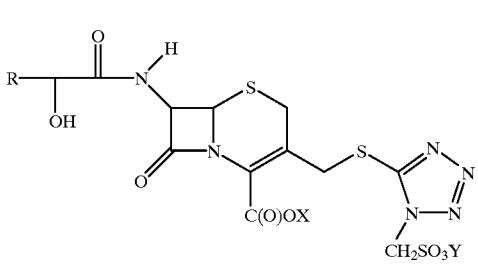

where R is any group which gives a compound having antibacterial activity and X is hydrogen or a pharmaceutically acceptable cation and Y is a pharmaceutically acceptable cation, which process comprises treating a compound of formula II,

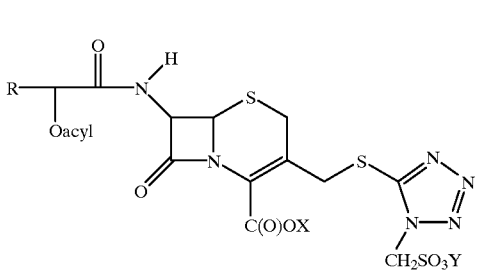

where X is hydrogen or a pharmaceutically acceptable cation, and Y is a pharmaceutically acceptable cation and "acyl" is an ester-forming group with an esterase or a lipase active in a pH range of about 3.5 to 8.0, using conditions under which the enzyme is able to hydroxyze the acyl group to form the alcohol.

DESCRIPTION OF THE INVENTION

While the process of this invention is illustrated by the compound 7-D-mandelamido-3-(α-sulfomethyltetrazol-5-ylthiomethyl)-3-cephem-4-carboxylic acid, it can be applied to any other cephalosporin having the -Oacyl group of formula (II). The term "acyl" is used here to designate any acyl group. Its scope is to include all esters which could be prepared for that designated hydroxyl group, and in particular, is to be viewed in light of the process for making compounds of formula I by the method set out in the Background section above. Specific esters of interest included not only the formyl ester, but other esters of 2 to 6 carbon atoms such as the acetate, propionate, butanoate, pentanoate or hexailoate esters or their isomeric forms.

The R group is specifically illustrated by a phenyl ring, which can be substituted if desired. Another group of R substituents are the 4, 5, 6 or 7-membered heterocycles. Heterocycles refers to substituted and unsubstituted, aromatic and non-aromatic groups containing one or more (preferably 1, 2 or 3) nitrogen, oxygen or sulfur atoms. Exemplary substituents are oxo (=O), halogen, hydroxy, nitro, amino, cyano, trifluoromethyl, alkyl of 1 to 4 carbons, alkoxy of 1 to 4 carbons, alkylsulfonyl, phenyl, substituted phenyl, 2-furfurylideneamino, benzylideneamino and substituted alkyl groups (wherein the alkyl group has 1 to 4 carbons).

A preferred sub-type of the 4, 5, 6 or 7-membered heterocycle group is the heteroaryl group. The term "heteroaryl" refers to those 4, 5, 6 or 7-membered heterocycles which are aromatic. Exemplary heteroaryl groups are substituted and unsubstituted pyridinyl, furanyl, pyrrolyl, thienyl, 1,2,3-triazolyl, 1,2,4-triazolyl, imidazolyl, thiazolyl, thiadiazolyl, pyrimidinyl, oxazolyl, triazinyl, and tetrazolyl. Exemplary nonaromatic heterocycles (i.e., fully or partially saturated heterocyclic groups) are substituted and unsubstituted azetidinyl, oxetanyl, thietanyl, piperidinyl, piperazinyl, imidazolidinyl, oxazolidinyl, pyrrolidinyl, tetrahydropyrimidinyl, dihydrothiazolyl and hexahydroazepinyl. Exemplary of the substituted 4, 5, 6 or 7-membered heterocycles are 1-alkyl-3-azetidinyl, 2-oxo-1-imidazolidinyl, 3-alkylsulfonyl-2-oxo-1-imidazolidinyl, 3-benzylideneamino-2-oxo-1-imdazolidinyl, 3-alkyl-2-oxo-1-imidazolidinyl, 3-phenyl (or substituted phenyl)-2-oxo-1-imidazolidinyl, 3-benzyl-2-oxo-1-imidazolidinyl, 3-(2-aminoethyl)-2-oxo-1-imidazolidinyl, 3-amino-2-oxo-1-imidazolidinyl, 3-[(alkoxycarbonyl)amino]-2-oxo-1-imidazolidinyl, 3-[2-[(alkoxycarbonyl)amino]ethyl]-2-oxo-1-imidazolidinyl, 2-oxo-1-pyrrolidinyl, 2-oxo-3-oxazolidinyl, 4-hydroxy-6-methyl-2-pyrimidinyl, 2-oxo-1-hexahydroazepinyl, 2-oxo-3-pyrrolidinyl, 2-oxo-3-tetrahydrofuranyl, 2,3-dioxo-1-piperazinyl, 2,5-dioxo-1-piperazinyl, 4-alkyl-2,3-dioxo-1-piperazinyl, or 4-phenyl-2,3-dioxo-1-piperazinyl.

Methods for making these compounds can be found in the patent and general scientific literature. The cephalosporin art discloses many methods for making cephalosporins, methods which could be utilized to make compounds of formula II either by working directly from the methods set out in those references, by combining those methods with the synthetic methods disclosed in U.S. Pat. Nos. 4,048,311 and 4,576,937 as illustrated for preparing formula (B) from (C), by a combinaton of these methods or by methods generally known in this art.

It is expected that this hydrolytic process will work with all types of compounds having an ester as illustrated formula II so long as they are stable and can be acted on by the enzyme in the pH range of about 3.5 to 8.0. These include pharmaceutically acceptable salt(s) such as those referred to or set out in U.S. Pat. No. 4,576,937 and its predecessor case U.S. Pat. No. 4,048,311.

Hydrolases affect hydrolysis of C—O and C—N bonds, in the process consuming a mole of water by virtue of adding a hydrogen to the oxygen or nitrogen and an —OH group to the carbon. The International Enzyme Commission has divided hydrolases into six groups characterized by the ability of the enzyme to hydrolyze esters, glycosidic bonds, peptide bonds, other C—N bonds and acid anhydrides. Esterases and lipases are believed to be the most useful in this invention.

It is believed that esterases and lipases, which are capable of hydrolyzing benzyl esters or mandelic acid esters and which retain at least 10% of their activity in the specific pH range, will function in this invention. It is most preferable that the selected enzyme retain at least 50% or more of its activity in the specified pH range. A review of esterases and lipases can be found in the publications, "Present and Future Applications of Lipases"—A. R. Macrae and R. C. Hammond, Biotech. Bioeng. Rev. 3, 193–217 (1985); P. Cesnuelle, The Enymes (P. D. Boyer, Ed.), Academic Press, New York, pp. 575–616 (1972) and K. Kirsch, The Enzymes P. D. Boyer, Ed.), Academic Press, New York, pp. 43–69 (1971)

Process conditions used herein will be those under which the enzyme is functional. This means that, aside from pH, solvents, temperature, salts, co-factors, coenzymes and the like will be employed in such a manner as to insure the catalysis will proceed in a useful fashion. Specific enzymes will have specific conditions under which they are most active. Not all such conditions can be recited in this writing because of the very substantial number of esterases and lipases which have been identified and characterized. Useful, and optimal, conditions for particular enzymes can be obtained from a number of compendia and the scientific literature. For example, a series such as Methods in Enzymology, provide directions and conditions for using many esterases and lipases. Other books like those published by the International Union of Biochemistry give citations to numerous enzymes where can be found conditions for their use. Such texts provide a source of information for esterases and lipases which would be expected to be useful in this invention.

Aqueous solutions are expected to be the most useful medium for carrying out the process of this invention. The reaction will be run at a temperature where the enzyme is functional. That temperature will depend on the particular characteristics of a given enzyme but generally is expected to be between about ambient temperature and 80° to 90° C. Preferred temperature ranges are between ambient and 37° C. Solution pH will depend on and be controlled by the pH range in which the operating range of the selected enzyme. Co-factors, co-enzymes, salts, all will depend on the characteristics of a particular enzyme.

Enzymes, not being consumed in the reaction, may be used in minor amounts relative to the substrate, the ester. No specific quantity of enzyme is required other than a quantity sufficient to effect hydrolysis of essentially all the substrate in a reasonable time under a set of given conditions. Appropriate quantities of enzyme can be determined by well known means with routine experimentation. The enzyme may be suspended or dissolved in the solution containing the substrate. An alternative means is to attach the enzyme to a support which is placed in the solvent. When the enzyme is attached to a solid support, the reaction can be effected by passing the substrate past the solid support in a continuous process or a batch process may be used where the support/enzyme is simply mixed in a container with the dissolved substrate. While gas or solid phase enzymatic processes are known, it is not expected that such processes will be a preferred means for practicing this invention.

Once the hydrolysis is completed, the product can be recovered by any means known in the art. Preferred conditions are set out in the following Examples. Other means for isolating and purifying the alcohol can be found in U.S. Pat. Nos. 4,048,311 and 4,576,937.

In order to identify the enzymes that are capable of hydrolyzing the formyl intermediate, the enzymes were incubated individually with II in phosphate buffer at pH 7. Four enzyme preparations (acetyl esterase from orange peel, lipases from wheat germ and Aspergillus niger and Subtilisin (A) were found to be suitable for the production of cefonicid sodium. It is expected that other esterase and lipase preparations will afford the same or similar results when used in the same or a similar manner.

The reaction was brought about by mixing the enzyme with a solution of formyl intermediate, preferably in the pH range of 5 to 8. The pH of the reaction medium was maintained constant through the periodic addition of alkali. The formyl intermediate could be provided either as the purified or unpurified form. Suitable concentration of the formyl intermediate is from 1 to 10%, and the suitable enzyme concentration is from 0.25 to 1% by weight. Reaction time and the total cefonicid sodium yield depend on such factors as concentration of the formyl intermediate, enzyme levels, temperature, and pH. By adjusting these conditions, quantitative production of cefonicid sodium was achieved at neutral pH.

EXAMPLE 1

Preparation of Formyl Intermediate

A suspension of 4.3 g of cephalosporanic acid derivative II in 20 ml of nanopure water was cooled in an ice bath. Sodium bicarbonate (1.87 g) in 7.5 ml of nanopure water was added dropwise (in 10 min) to the cephalosporanic acid (II) suspension with stirring and cooling. O-Formylmandaloyl chloride (2.26 ml) was then added dropwise with stirring. The reaction mixture was stirred for an additional 45 to 60 min. It was then acidified to pH 2.5 with concentrated hydrochloric acid. The acidified mixture was extracted first with 20 ml and then with 10 ml of HPLC-grade ethyl acetate.

Enzyme Reaction

The acidified, ethyl acetate-extracted, aqueous phase was cooled in an ice bath and the pH was raised through the careful addition of 20% sodium hydroxide solution, with vigorous stirring. When the pH neared 6 to 6.5, 85 mg mono-, di- or tri- sodium phosphate (anhydrous) was added and 0.5 M sodium carbonate solution was used to raise the pH to 7.5. The reaction mixture was taken out of the ice bath and was allowed to warm to 20° C. Lipase from Aspergillus niger (200 mg) was suspended in 1 ml of reaction mixture and added. The pH was maintained between 7.35 to 7.5 through the addition of 0.5 M sodium carbonate solution. Samples were taken at different time intervals and analyzed by HPLC.

In the HPLC analysis, the reaction product had the same retention time as an authentic sample of cefonicid sodium prepared as described in U.S. Pat. No. 4,576,937. The yield of cefonicid sodium was quantitative as determined by HPLC analysis.

EXAMPLE 2

Twenty mls. of 16% (w/v) O-formyl cefonicid were adjusted to pH 7.0 with 0.5 m sodium carbonate. To this was added 50 mg. Subtilisin A (Novo, Nordisk) and the pH was maintained at 7.0 with 0.5 m sodium carbonate during the de-blocking reaction which was carried out at 20° over 50 minutes to provide cefonicid at 92.9% yield.

The foregoing discussion and Example illustrate how to perform the invention. But this information is not set out to limit the invention, just to illustrate how to practice it. What is reserved to the inventors is recited in the claims herein.

We claim:

1. A process for preparing a compound of the formula:

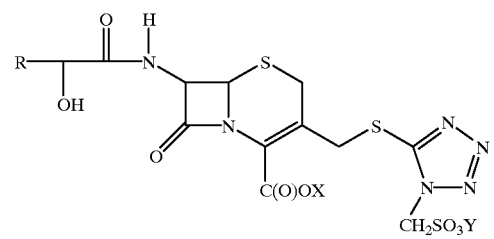

where R is substituted or unsubstituted phenyl, substituted or unsubstituted heterocyclyl, or substituted or unsubstituted heteroaryl, X is hydrogen or a pharmaceutically acceptable cation and Y is a pharmaceutically acceptable cation, which process comprises treating a compound of the formula:

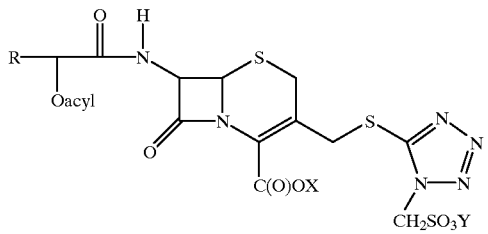

where X is hydrogen or a pharmaceutically acceptable cation, Y is a pharmaceutically acceptable cation and acyl is an ester-forming group with an esterase or a lipase active in a pH range of about 3.5 to 8.0, using conditions under which the enzyme is active, to hydrolyze the acyl group to form the alcohol, such that the target compound is produced.

2. The process of claim 1 where the esterase is acetyl esterase from orange peel.

3. The process of claim 1 where the lipase is from wheat germ.

4. The process of claim 1 where tile lipase is obtained from *Aspergillus niger*.

5. The process of claim 1 where R is phenyl.

6. The process of claim 5 where the esterase is acetyl esterase obtained from orange peel and X and Y are sodium.

7. The process of claim 5 where the lipase is obtained from wheat germ and X and Y are sodium.

8. The process of claim 5 where the lipase is obtained from *Aspergillus niger* X and Y are sodium.

9. A process for preparing a compound of the formula:

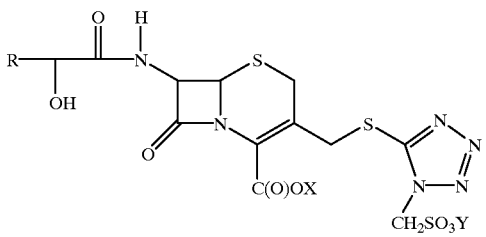

where R is substituted or unsubstituted phenyl, substituted or unsubstituted heterocyclyl, or substituted or unsubstituted heteroaryl, X is hydrogen or a pharmaceutically acceptable cation and Y is a pharmaceutically acceptable cation, which process comprises treating a compound of the formula:

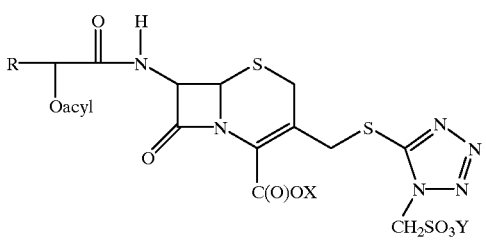

where X is hydrogen or a pharmaceutically acceptable cation, Y is a pharmaceutically acceptable cation and acyl is an ester-forming group with Subtilisin A, using conditions under which the Subtilisin A is active, to hydrolyze the acyl group to form the alcohol, such that the target compound is produced.

10. The process of claim 9 where R is phenyl.

11. The process of claim 10 where X and Y are sodium.

* * * * *